United States Patent [19]

Orser et al.

[11] Patent Number: 4,464,473

[45] Date of Patent: Aug. 7, 1984

[54] ICE NUCLEATING MICROORGANISMS

[75] Inventors: Cindy S. Orser; Steven E. Lindow, both of Berkeley; Nickolas J. Panopoulos, Oakland; Brian J. Staskawicz, Castro Valley, all of Calif.

[73] Assignee: The Regents of the University of California, Berkeley, Calif.

[21] Appl. No.: 371,162

[22] Filed: Apr. 23, 1982

[51] Int. Cl.$^3$ .................. C12N 15/00; C12N 1/20; C12N 1/00; C12P 21/00; C07H 21/04
[52] U.S. Cl. .................................. 435/172.3; 435/68; 435/253; 435/317; 935/72; 935/9; 935/64; 935/26; 935/28; 536/27
[58] Field of Search .................. 435/68, 70, 172, 253, 435/317, 240, 241; 536/27

[56] References Cited
PUBLICATIONS

Lindow et al., Applied and Environmental Microbiology 36, 831 (1978).
Helling et al., in *Genetic Engineering,* Chakrabarty (ed.), CRC Press, 1978, pp. 1-30.
Hohn, Methods in Enzymology, vol. 68, pp. 299-309 (1979).
Lindow et al., *Proc. Am. Phytopathol. Soc.* (1977) 4:169.
Arny et al., *Nature* (1976) 262:282-284.
Lindow et al., *Phytopathology* (1978) 68:523-527.
Lindow et al., *Proc. Am. Phytopathol. Soc.* (1977) 3:224.
Lindow et al., Applied and Environmental Microbiology 36, 831 (1978).

*Primary Examiner*—Thomas G. Wiseman
*Assistant Examiner*—James Martinell
*Attorney, Agent, or Firm*—Bertram I. Rowland

[57] ABSTRACT

DNA sequences encoding for ice nucleation activity are isolated and introduced into unicellular hosts. The modified hosts demonstrate ice nucleation activity analogous to the DNA source host. The cellular products find use in inhibiting supercooling.

13 Claims, No Drawings

ICE NUCLEATING MICROORGANISMS

BACKGROUND OF THE INVENTION

1. Field of the Invention

Genetic evolution has afforded an extraordinary array of biological capabilities in nature. The various organisms or cells achieve these different functions by producing a wide variety of proteins, many of which in turn can produce a wide variety of non-proteinaceous molecules. These naturally occurring compounds can interact with their environment modifying the environment for good and bad.

It has been found that certain organisms are capable of nucleating the formation of ice. Ice nucleation is of substantial commercial interest as a factor in inducing frost injury to plants, in atmospheric precipitation processes and in commercial snowmaking. Therefore, the ability to control the ice nucleating capability of microorganisms or to produce products having such nucleation capability can be employed in a wide range of agricultural, commercial, recreational or environmental situations. The ice nucleating microorganisms can be used for preventing supercooling of water, in snowmaking machines, in ice rinks, or other situations where supercooling is energy inefficient.

2. Description of the Prior Art

A variety of papers have been published concerning the effect of bacteria on ice nucleation. See, for example, Lindow et al., Proc. Am. Phytopathol. Soc. (1977) 4.1976:169; Arny et al., Nature (1976) 262:282–283; Lindow et al. Phytophathology (1978) 68:523–528; Lindow et al., Appl. Environ. Microbiol. (1978) 36:831–838; Lindow et al., Proc. Am. Phytopathol Soc. (1977) 3.1976:224. See also, U.S. Pat. Nos. 4,045,910, 4,161,084, and 4,200,228. See also, copending application Ser. No. 294,604, filed Aug. 20, 1981, and references cited therein.

SUMMARY OF THE INVENTION

DNA sequences encoding for substances having ice nucleation activity are provided. The sequences are capable of being cloned in a host foreign to the source of the DNA sequence and imparting ice nucleation activity to such host. DNA sequences, plasmids and transformants are described.

DESCRIPTION OF THE SPECIFIC EMBODIMENTS

The subject invention provides for the isolation of DNA segments encoding for ice nucleation activity (INA), which DNA segments may be introduced into an appropriate vector. The vector may be a plasmid, virus or other self-replicating extrachromosomal element which may be used for conjugation, transformation, transduction, or transfection for introduction of the INA activity into a unicellular microorganism host. The host may then be grown and cloned and INA+ clones isolated. The INA positive clones or subcellular portions or extracts derived from them may be used for ice nucleation in snowmaking (see U.S. Pat. No. 4,200,228), as a source of the protein(s) encoded by the INA encoding gene(s), as a source of other cellular substances resulting from the expression of said gene(s), or in other situations where water supercooling is undesirable.

In order to obtain the DNA sequence encoding for INA, an organism known to provide for ice nucleation may be employed. Conveniently, various species of Pseudomonas, such as *syringae, coronafaciens, pisi, tabaci* or *fluorescens,* Xanthomonas, such as *translucens,* or Erwinia, such as *herbicola,* or other organism having ice nucleation activity may be employed as a source for the preparation of a genomic library. Various restriction enzymes may be employed which provide for segments of up to 25 kb by complete or incomplete digestion. These fragments may then be cloned.

Various vectors may be employed having different specificities. Plasmids, viruses, or cosmids may be employed, which allow for insertion of the fragments from the genomic library to provide a functional self-replicating extrachromosomal element. Therefore, the vector should have a convenient restriction site or one should be able to introduce such site, which allows for a convenient insertion of the genomic library fragments. Desirably, the vector should provide a means for selection and/or screening, through antibiotic selection, packaging requirements, inactivation of a gene, or other means.

Of particular interest is a cosmid vector, more particularly pLAFR1, which has a unique EcoRI site. This vector is a derivative of the vector pRK290 (Tc$^r$) that contains the cos sites of phage λ for in vitro packaging. It is a broad host range oligocopy vector, where the unique EcoRI site is outside the Tc gene. There is no selection or screening for insertional inactivation in pRK290, however, the pLAFR1 derivative is very useful because packaging selects for inserts automatically, where the inserts are of about 20 kb±10 kb in length.

Depending upon the choice of vector, the DNA sequence encoding for INA may be introduced into a wide variety of unicellular microorganism hosts, including bacteria, fungi, yeast, algae, protozoa, and the like. The choice of host will depend upon the availability of a vector, the purpose for introducing the INA into the host, and the manner in which the host is to be used. Depending upon the nature of the vector, various techniques may be used for introducing the vector plus a DNA insert into the host. Transformation can be achieved in conventional ways employing calcium precipitated DNA in an appropriate solvent. Transfection may be achieved by contacting cells in nutrient medium with a modified virus or its DNA to cause transfection or transduction of the cells depending upon integration of the sequence encoding INA. Conjugation can also be employed, where the plasmid is introduced into one organism, which may then transfer the plasmid to a different organism either being capable of mobilization by itself or in conjunction with a mobilizing plasmid.

In isolating the organisms receiving the exogenous DNA from the genomic library, it is desirable to use a INA− organism, whereby a resulting clone which is shown to be INA+ is likely to have had a DNA sequence encoding for INA introduced into the organism. Many organisms do not naturally have INA capability, so that any clones which show ice nucleation capability would have had to have received the DNA encoding for INA.

Now that it has been shown that the genes encoding for INA can be transferred to organisms which had previously not shown ice nucleation capability, these organisms can now be used for screening DNA segments for INA activity. The clones can be screened by a simple technique where colonies plated on appropriate solid nutrient media are transferred to velvet pads which are replica-printed onto sheets of aluminum foil precoated with a thin layer of paraffin. By placing the sheets onto the surface of a circulating alcohol bath precooled to temperatures below zero and atomizing water over the sheets, so that microdroplets contact the cells, INA+ cells freeze the microdroplets and give a frosty appearance to INA+ colonies. In this manner, INA+ colonies can be identified.

It is found that the genes encoding INA activity can be located on a single fragment of less than about 10 kb. Thus, it is found that the genes involved with INA are not distributed at a number of different sites in the chromosome, nor does the product encoded by such genes require for INA activity the specific nature of the membrane associated with naturally occurring microorganisms having ice nucleating activity. Furthermore, ice nucleating capability is greatly enhanced by employing a multicopy vector, so that it appears that the ice nucleating activity is associated with enhanced expression of the genes encoding for the INA.

In order to demonstrate the subject invention, the following experiments were carried out.

EXPERIMENTAL

Methods

Three strains were employed as sources for DNA encoding for INA: *Pseudomonas syringae* (two strains:-cit-7 and 31rif-1) and *Erwinia herbicola* (one strain:26SR6-2). The DNA from the strains was extracted, purified by two cycles of CsCl-ethidium bromide density gradient centrifugation, freed of ethidium bromide, dialyzed against appropriate buffers, partially digested with EcoRI and fractionated by a 5-25 neutral sucrose gradient centrifugation. The partial digestion employed 0.3 units EcoRI per 1 μg DNA following the directions of the supplier (Bethesda, Research Laboratories, Md.) and the reaction quenched after 0.5 hr by heating at 65° C. for 2 min. Fractions obtained from the sucrose gradient were analyzed by agarose gel electrophoresis and those rich in fragments in the 18-25 kb range were pooled and ligated to the cosmid vector pLAFR1, previously linearized with EcoRI. (pLAFR1 was supplied by S. Long).

The plasmid pLAFR1 is a derivative of the vector pRK290 (Tc$^r$) that contains the cos sites of phage λ for in vitro packaging. pLAFR1 was obtained by inserting a BglII fragment from pHC79 (Hohn and Collins, Gene (1980) 11:291-298) into the BglII site of pRK290. The plasmid is a broad host range oligocopy vector with a single EcoRI site outside the Tc gene. There is no selection or screening for insertional inactivation in pRK290. However, the pLAFR1 derivative is very useful because it requires inserts of a minimum size for packaging and therefore selects automatically for inserts of about 18-30 kb in length.

Ligation of the DNA fragments in pLAFR1 is achieved using T4 ligase following the supplier's directions (Bethesda Research Labs.). A relatively high ratio of foreign DNA fragments to linearized vector is employed, about 3-4:1, to minimize dimerization of the vector. About 3-4 μg of DNA fragments is employed per 1 μg of linearized pLAFR1. The DNA fragments are ligated in buffer brought to 10 μl with water, after being heated for 5 min at 65° C., 30 min at 42° C. and then allowed to set for 2 hrs at room temperature. The annealed mixture is made 1 mM ATP and 1 unit T4 ligase added and the mixture incubated at 12° C. overnight.

The ligated mixture was packaged in vitro and transduced into E. coli HB101. Packaging is achieved in accordance with the procedure described by Hohn, M: In Vitro Packaging of λ and Cosmid DNA, Wu ed. Methods in Enzymology, vol. 68, Academic Press, N.Y., pages 299-309, 1979. Approximately 30 μl λ heads and 20 μl λ tails are combined with 2 μl 1M ATP and 5 μl ligation reaction mixture and the resulting mixture incubated for 1 hr at room temperature. To the mixture is then added buffer 10 mM tris, pH 7.16, 10 mM MgCl$_2$ to provide the phage stock which is employed for transduction.

The transduction was accomplished by combining 0.1 ml of the phage stock with 0.5 ml of E. coli HB101 (10$^7$-10$^8$ cells/ml, mid-log growth) in Luria broth 0.4% maltose, and incubating for one hour at 37° C. The mixture was diluted with 2 ml Luria broth and incubated for 1.5-2 hrs. The cells were then plated on agar medium (Luria agar) supplemented with tetracycline (10 μg/ml) and incubated for 1-2 days.

The colonies on several of the plates were screened for ice nucleation activity (INA) by transferring to velvet pads which were replica-printed onto sheets of aluminum foil precoated with a thin coating of paraffin. The foils were bent upwards at the edges, placed on a circulating alcohol-bath, adjusted to −5° and −9° C. and the cells on the paraffin-coated foil sprayed with water microdroplets. Microdroplets that are in contact with INA+ cells freeze, giving a frosty appearance to INA+ colonies. Several INA+ colonies were identified in each library and purified.

The spectrum or profile of ice nuclei to temperature is determined by placing a plurality of bacteria-containing water droplets (10 μl) on a paraffin-coated temperature controlled aluminum block, where the temperature is slowly lowered (~0.2° C./min) and the cumulative number of droplets which freeze are counted. The number of cells per droplet can be varied by serial dilution. The number of ice nuclei is calculated from the number of frozen droplets at each temperature and is plotted against temperature at various cell concentrations. The log of ice nuclei/cell is plotted against temperature and usually shows two plateaus, one in the region of −4° to −7° C. and one below −9° C.

Results

All INA+ E. coli transductants contained recombinant plasmids, each having a different EcoRI fragment, but with one common fragment corresponding to the vector used in the plasmid construction. Some of the recombinant plasmids were introduced into E. coli (SK1592) and HB101 and to INA− mutants of the "DNA source strain" used in their construction (*P. syringae*, cit-7 and *E. herbicola* 26SR6-2) by transformation and/or mobilization. In all cases INA+ progeny were obtained. The above results demonstrate that the cloned DNA fragments encode for expression of the INA+ phenotype in the strains of origin and are capable of expressing the phenotype in a heterologous INA− cellular environment, such as E. coli.

A particular plasmid pC-1 was isolated and used in a number of experiments. pC-1 contained a 23.2 kb partially digested EcoRI fragment from the strain *P. syringae* cit-7 and inserted into the unique EcoRI site of pLAFR1. The ice nucleation spectrum (see Methods) of E. coli carrying the plasmid pC-1 was compared with that of *P. syringae* cit-7 strain and the spectra found to be essentially identical. A 10 kb EcoRI fragment from the pC-1 insert was subcloned in the unique EcoRI site of the multicopy vector pBR325. This site is in the chloramphenicol acetyltransferase gene. The resulting plasmid, designated pC1BR1 upon EcoRI restriction showed the restriction fragments expected of pBR325 carrying a single EcoRI insert (approximately 10 kb) which was present in pC-1 and confers INA+ phenotype to E. coli. The frequency of ice nucleation (cell/nuclei) by E. coli HB101 (pC-1) and E. coli HB101 (pC1BR1) after growth at 23° C. (optimal for expression of INA in wild type strains) and at 37° C. was compared. (Although wild type P. syringae does not grow at 37° C., it is known that growth temperatures higher than 24° C. strongly reduce ice nucleation frequency.) Cells were assayed for ice nucleation frequency after 24 and 49 hours of growth (expression of INA wild type INA+ strains increases greatly at late states of growth cycle). The following table indicates the results.

TABLE 1

|  | cells/nuclei | |
| --- | --- | --- |
|  | −5° C.+ | −9° C.+ |
| P. syringae* Cit 7 | 4.13E2 | 1.92E2 |
| E. coli HB101 (pC-1) | 1.43E4 | 2.56E2 |
| E. coli HB101 (pCIBR1) | 5.65E1 | 2.07 |
| E. herbicola* 26SR6-2 | 5.247E5 | 7.27E2 |
| E. coli HB101 (pE-7)$^o$ | 8.27E3 | 9.02E2 |
| E. coli HB101* — | 0 | 0 |

48 hour old cultures grown on KB Tc ($_{15\ \mu g/ml}$) or KB* (KB = Kings B medium) +Ej = 10$^j$
$^o$ pLAFR1 with E. herbicola DNA fragment The above data indicate that: (1) the expression of INA activity in E. coli is under similar temperature and temporal control as in wild type strains; and (2) cloning in a multicopy vector results in substantially greater ice nucleation frequency (i.e. a much greater proportion of cells result that contain active ice nuclei). Based on these experiments, this affect cannot be exclusively attributed to the "copy number effect," resulting in more efficient expression of the cloned genes (the EcoRI fragment and pC1BR1 is inserted within the chloramphenicol acetyltransferase encoding sequence of pBR325) or to the elimination of repressor-type regulatory elements during the subcloning of the active fragment from pC-1. The level of expression of INA in E. coli HB101 (pC1BR1) is 2 cells/nuclei, which is at or near the limit of the assay methods used.

It is evident from the above results that ice nucleation activity can be transferred to a wide range of hosts which have previously not had this capability. This does not preclude the introduction of said DNA fragments to INA+ hosts to obtain for example, increased expression of INA through the use of a multicopy vector. A relatively small DNA fragment is required which can easily be introduced into a wide range of organisms and cells, either in single or multicopy form, either remaining extrachromosomal or being integrated, and providing for INA+ phenotype. Thus, organisms which have a wide variety of ecological niches can be modified so as to provide for ice nucleation activity in new environments and/or with higher efficiency. Organisms that are more efficient with respect to INA expression are also attractive candidates for use for weather modification.

Although the foregoing invention has been described in some detail by way of illustration and example for purposes of clarity of understanding, it will be obvious that certain changes and modifications may be practiced within the scope of the appended claims.

What is claimed is:

1. A bacterial cell having ice nucleation activity as a result of introducing into said cell or a parent of said cell a heterologous DNA sequence derived from Pseudomonas, Erwinia, or Xanthomonas microorganism encoding for ice nucleation activity or a heterologous DNA sequence encoding for ice nucleation activity and substantially homoduplexing with said DNA derived from said microorganism.

2. A bacterial cell according to claim 1, wherein said DNA sequence is on an extrachromosomal element.

3. The cell of claim 1, said cell being E. coli.

4. E. coli according to claim 3, wherein said ice nucleation activity results from a gene carried on an extrachromosomal element.

5. A DNA sequence of less than 10 kb encoding for ice nucleation activity and substantially homoduplexing with ice nucleation activity encoding DNA derived from Pseudomonas, Erwinia or Xanthomonas.

6. A DNA sequence according to claim 5, wherein said sequence is derived from the species Pseudomonas or Erwinia or Xanthomonas.

7. A functional self-replicating extrachromosomal element having an intact replicon and a DNA sequence capable of expression, according to claim 5.

8. An element according to claim 7, wherein said replicon is recognized by a bacterial host.

9. An element according to any of claims 7 or 8, wherein said DNA sequence is derived from Pseudomonas or Erwinia.

10. A method for conferring ice nucleation activity on a bacterial cell, which comprises: introducing into said cell DNA comprising a DNA sequence of less than 10 kb encoding for ice nucleation activity and substantially homoduplexing with ice nucleation activity encoding DNA derived from Pseudomonas, Erwinia or Xanthomonas under conditions where said DNA sequence is expressed; and growing cells which contain said DNA sequence.

11. A method according to claim 10, wherein said DNA sequence is a plasmid insert and is introduced by transformation as part of said plasmid.

12. A method according to claim 10, wherein said DNA sequence is a cosmid insert and is introduced by transduction as a part of said cosmid.

13. A method according to claim 12, wherein said cell is E. coli.

* * * * *

UNITED STATES PATENT AND TRADEMARK OFFICE
CERTIFICATE OF CORRECTION

PATENT NO. : 4,464,473

DATED : Aug. 7, 1984

INVENTOR(S) : Orser et al.

It is certified that error appears in the above-identified patent and that said Letters Patent is hereby corrected as shown below:

Title page, Item [73] should read as follows:

-- Assignee: The Regents of the University of California, Berkeley, Calif. and, International Genetic Engineering, Inc., Santa Monica, Calif. --.

Signed and Sealed this

Thirtieth Day of April 1985

[SEAL]

Attest:

DONALD J. QUIGG

Attesting Officer

Acting Commissioner of Patents and Trademarks